United States Patent
Athey et al.

(12) 
(10) Patent No.: US 6,288,263 B1
(45) Date of Patent: Sep. 11, 2001

(54) INTERMEDIATES FOR THE PREPARATION OF N-[2-(CARBOXYMETHOXY)ETHYL]-N-(CARBOXYMETHYL)GLYCINE

(75) Inventors: Phillip S. Athey; David A. Wilson, both of Lake Jackson, TX (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/579,400

(22) Filed: May 25, 2000

Related U.S. Application Data

(60) Provisional application No. 60/139,420, filed on Jun. 16, 1999.

(51) Int. Cl.⁷ ............... C07C 255/03; C07C 229/10
(52) U.S. Cl. ................. 558/441; 558/442; 562/568
(58) Field of Search .................. 558/441, 442; 562/568

(56) References Cited

U.S. PATENT DOCUMENTS

| | | | |
|---|---|---|---|
| 2,833,751 | * 5/1958 | Luskin et al. | 260/85.5 |
| 5,051,212 | 9/1991 | Culshaw et al. | 252/546 |
| 5,191,106 | 3/1993 | Parker | 552/346 |
| 5,907,055 | 5/1999 | Greindl et al. | 562/526 |

FOREIGN PATENT DOCUMENTS

| | | | |
|---|---|---|---|
| 1 513 550 | 6/1978 | (GB) | C11D/10/02 |
| 94/12606 | 6/1994 | (WO) | C11D/3/32 |

OTHER PUBLICATIONS

International Search Report dated Feb. 7, 2001 issued by the EPO acting as the International Searching Authority in PCT/US00/14504.

* cited by examiner

Primary Examiner—Joseph K. McKane
Assistant Examiner—Ebenezer Sackey

(57) ABSTRACT

Compounds represented by the formula

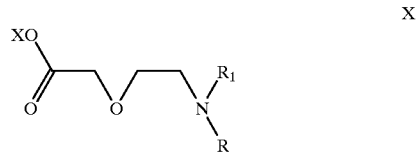

wherein R and $R_1$ independently represent H, —$CH_2CN$ or —$CH_2CO_2X$, with the proviso that R and $R_1$ can not be both H or —$CH_2CO_2X$; and X represents hydrogen, an alkali metal or alkaline earth metal are disclosed. These compounds are useful as intermediate compounds in the preparation of N-[2-(carboxymethoxy)ethyl]-N-(carboxy-methyl) glycine. These intermediates can be formed by contacting 3-morpholinone with glycolonitrile under alkaline conditions to form an aminonitrile which can be hydrolyzed and contacted with additional glycolonitrile to form the nitrile intermediate which can be converted to N-[2-(carboxymethoxy)ethyl]-N-(carboxymethyl)glycine via hydrolysis.

7 Claims, No Drawings

INTERMEDIATES FOR THE PREPARATION OF N-[2-(CARBOXYMETHOXY)ETHYL]-N-(CARBOXYMETHYL)GLYCINE

CROSS-REFERENCE STATEMENT

This application claims the benefit of U.S. Provisional Application No. 60/139,420 filed Jun. 16, 1999.

BACKGROUND OF THE INVENTION

The present invention concerns intermediate compounds useful in the preparation of N-[2-(carboxymethoxy)ethyl]-N-(carboxymethyl)glycine (CMHEIDA), also referred to as carboxymethoxyhydroxyethylimino diacetic acid.

Chelants or chelating agents are compounds which form coordinate-covalent bonds with a metal ion to form chelates. Chelates are coordination compounds in which a central metal atom is bonded to two or more other atoms in at least one other molecule or ion, called a ligand, such that at least one heterocyclic ring is formed with the metal atom as part of each ring.

Chelating agents for metal ions, such as calcium, magnesium, iron, and magnesium, are required for a wide range of technical fields. Examples of fields of application and end-uses of chelants are detergents, in electroplating, in water treatment, photography, textile industry, paper industry and also various uses in pharmaceuticals, cosmetics, foodstuffs and plant nutrition. Some of these activities may result in the chelating agents entering the environment. For example, agricultural uses or use in detergents may result in measurable quantities of the chelants in water.

As chelants many enter the environment from various uses, it is desirable to have chelants that would readily degrade after use. It would be particularly advantageous to have a chelant which is biodegradable, that is, susceptible to degradation by microbes which are generally naturally present in environments into which the chelants may be introduced.

Iminodiacetic acid derivatives are known to possess metal sequestering properties. US patent 5,051,212 discloses that iminodiacetic acid derivatives, when combined with organic solvents, provide very good results in terms of soil removal from hard surfaces. The use of iminodiacetic acid derivatives in aqueous compositions for cleaning hard surfaces is reported in PCT Application No. WO 94/12606. The iminodiacetic acid derivatives in WO 94/12606 are also reported to have good biodegradable characteristics.

SUMMARY OF THE INVENTION

The present invention concerns compounds represented by the formula

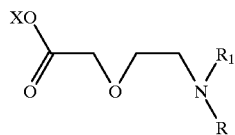

wherein R and $R_1$ independently represent H, —$CH_2CN$ or —$CH_2CO_2X$, with the proviso that R and $R_1$ can not be both H or —$CH_2CO_2X$; and X represents hydrogen, an alkali metal or alkaline earth metal.

In another aspect, the present invention concerns a process for the preparation of N-[2-(carboxymethoxy)ethyl]aminoacetonitrile (III) which process comprises alkylating 3-morpholinone with formaldehyde and hydrogen cyanide or glycolonitrile under alkaline conditions.

Still in another aspect, the present invention concerns a process for the preparation of N-[2-(carboxymethoxy)ethyl] glycine (V) which process comprises hydrolyzing an aqueous solution of a compound of the formula:

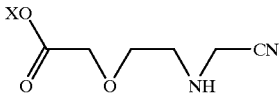

III wherein X is hydrogen or an alkali or alkaline-earth metal with an acid or base.

Still in another aspect, the present invention concerns a process for the preparation of N-[2-(carboxymethoxy)ethyl]-N-(carboxymethyl)glycine (Formula IX) which process comprises hydrolyzing an aqueous solution of a compound of the formula:

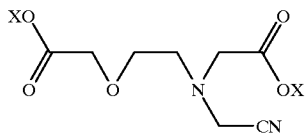

VII wherein X is hydrogen or an alkali or alkaline-earth metal with an acid or base.

In another aspect, the present invention concerns a process for the preparation of N-[2-(carboxymethoxy)ethyl]-N-(carboxymethyl)glycine (IX) which process comprises reacting (2-aminoethoxy)acetic acid with glycolonitrile or hydrogen cyanide and formaldehyde under alkaline conditions.

Still in another aspect, the present invention concerns a process for the preparation of N-[2-(carboxymethoxy)ethyl]-N-(carboxymethyl)glycine (IX) which process comprises reacting (2-aminoethoxy)acetic acid with hydrogen cyanide and formaldehyde under acidic conditions followed by hydrolysis.

Yet in another aspect, the invention concerns a multi step process for the preparation of N-[2-(carboxymethoxy)ethyl]-N-(carboxymethyl)glycine (IX) which process comprises the steps of (1) reacting 3-morpholinone with a base to form (2-aminoethoxy)acetic acid (Ib);

(2) alkylating (2-aminoethoxy)acetic acid salt formed in step (1) with formaldehyde to form [2-(hydroxymethylamino)ethoxy]acetic acid (II);

(3) reacting [2-(hydroxymethylamino)ethoxy]acetic acid salt formed in step (2) with hydrogen cyanide to form [2-(cyanomethylamino)ethoxy]acetic acid (III);

(4) hydrolysing [2-(cyanomethylamino)ethoxy]acetic acid formed in step (3) with a base to form N-[2-(carboxymethoxy)ethyl]glycine salt (V);

(5) reacting N-[2-(carboxymethoxy)ethyl]glycine formed in step (4) with formaldehyde and hydrogen cyanide to form N-[2-(carboxymethoxy)ethyl]-N-(cyanomethyl) glycine (VII); and (6) hydrolysing N-[2-(carboxymethoxy)ethyl]-N-(cyanomethyl)glycine formed in step (5) with a base to form N-[2-(carboxymethoxy)ethyl]-N-(carboxymethyl)glycine (IX).

This process is illustrated in Scheme I below.

Yet in another aspect, the present invention relates to aqueous hard surface cleaning compositions comprising N-[2-(carboxymethoxy)ethyl]-N-(carboxymethyl)glycine (IX).

Still in another aspect, the present invention concerns a method of cleaning a hard surface by contacting said hard surface with an aqueous hard surface cleaning composition comprising N-[2-(carboxymethoxy)ethyl]-N-(carboxymethyl)glycine (IX).

DETAILED DESCRIPTION OF THE INVENTION

The compounds of the present invention represented by the formula

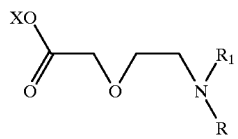

X wherein R and $R_1$ independently represent H, —$CH_2CN$ or —$CH_2CO_2X$, with the proviso that R and $R_1$ can not be both H or —$CH_2CO_2X$; and X represents hydrogen, an alkali metal or alkaline earth metal are useful as intermediates in the synthesis of N-[2-(carboxymethoxy)ethyl]-N-(carboxymethyl)glycine (IX).

One preferred embodiment of the compounds of the present invention is represented by the formula

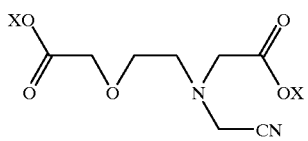

VII wherein X represents hydrogen, an alkali metal or alkaline earth metal.

Still another preferred embodiment of the compounds of the present invention is represented by the formula

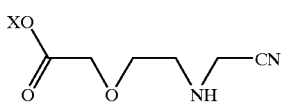

III wherein X represents hydrogen, an alkali metal or alkaline earth metal.

Yet another preferred embodiment of the compounds of the present invention is represented by the formula

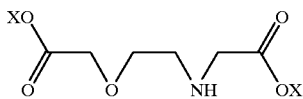

wherein X represents hydrogen, an alkali metal or alkaline earth metal.

Starting materials for making the intermediate compounds of the present invention of formula IX include 3-morpholinone and hydrogen cyanide and formaldehyde, or glycolonitrile. A suitable reaction scheme for the synthesis of the intermediate compounds of the present invention is shown in Scheme I below.

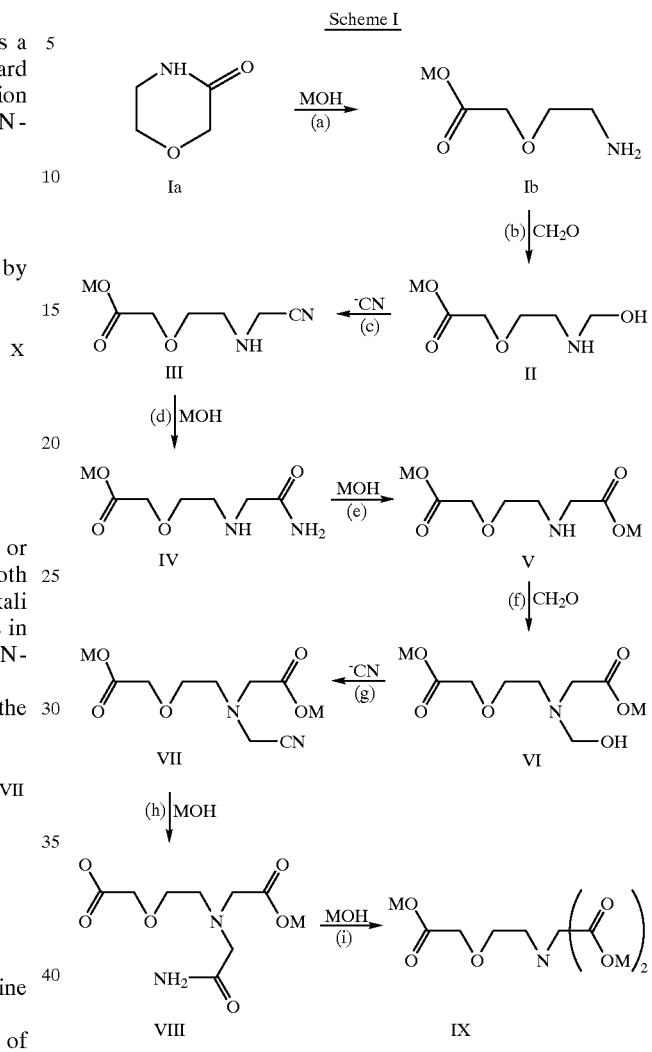

Scheme I

M in Scheme I independently in each occurrence represents an alkali or alkaline-earth metal.

In the multi step process of the present invention 3-morpholinone (Ia) is first contacted with a suitable base such as sodium hydroxide, followed by alkylation with formaldehyde and hydrogen cyanide to form [2-(cyanomethyl-amino)ethoxy]acetic acid (III). The molar ratio of 3-morpholinone (Ia) to formaldehyde and hydrogen cyanide is generally about 1:1.

The hydrolysis of [2-(cyanomethylamino)ethoxy]acetic acid (III) with a base gives N-[2-(carboxymethoxy)ethyl] glycine (V).

N-[2-(carboxymethoxy)ethyl]glycine (V) is then reacted with additional formaldehyde and hydrogen cyanide to form N-[2-(carboxymethoxy)ethyl]-N-(cyanomethyl)glycine (VII). The molar ratio of N-[2-(carboxymethoxy)ethyl] glycine (V) to formaldehyde and hydrogen cyanide is generally about 1:1.

In the above reactions, glycolonitrile can be substituted for formaldehyde and hydrogen cyanide.

N-[2-(carboxymethoxy)ethyl]-N-(cyanomethyl)glycine (VII) is then hydrolyzed using a base such as sodium hydroxide to give the alkali metal salt of N-[2-(carboxymethoxy)ethyl]-N-(carboxymethyl)glycine (IX).

Hydrolysis of the cyanomethyl group proceeds through the amide intermediate as depicted by structure (VIII) in Scheme I, resulting in the formation of the carboxymethyl group, which liberates the easily removable ammonia.

The above reactions may be carried out in the presence of any base capable of hydrolyzing the nitrile functionality. Examples of suitable bases include alkali and alkaline earth metal hydroxides. Preferably sodium and potassium hydroxide are used in the above reaction scheme.

In addition to bases, the nitrile functionality can be hydrolyzed using strong acids such as hydrochloric acid or sulfuric acid. In this case, the ammonium salt of the respective acid is obtained as a by-product.

While reaction Scheme I shows the addition of one mole equivalent of base per mole of nitrile functionality, excess molar amounts of base can be used.

Preferably the alkylation reaction steps are carried out at a temperature from about 0 to 100° C., preferably from about 15 to 65° C. The hydrolysis of N-[2-(carboxymethoxy)ethyl] aminoacetonitrile (III) and N-[2-(carboxymethoxy)ethyl]-N-(cyanomethyl)glycine (VII) is generally done at a temperature from about 0 to about 120° C. Preferably the hydrolysis step is done at a temperature from about 20° C. to about 105° C.

The hydrolysis of N-[2-(carboxymethoxy)ethyl]-N-(cyanomethyl)glycine (VII) to N-[2-(carboxymethoxy) ethyl]-N-(carboxymethyl)glycine (IX) results in a conversion in excess of 90 percent. Although Scheme I indicates that the production of N-[2-(carboxymethoxy)ethyl]-N-(carboxymethyl)glycine (IX) is done in step reactions, the production can be accomplished by adding glycolonitrile to an alkaline solution of 3-morpholinone (Ia) at a temperature to achieve alkaline hydrolysis. In this procedure, intermediate N-[2-(carboxymethoxy)ethyl]-N-(cyanomethyl) glycine (VII) is rapidly converted to N-[2-(carboxymethoxy)ethyl]-N-(carboxymethyl)-glycine (IX).

N-[2-(carboxymethoxy)ethyl]-N-(carboxymethyl)glycine is a chelant which will biodegrade in the semi-continuous activated sludge test (ASTM D-2667). In this test, a standardized sludge containing municipal waste treatment plant organisms is used to biodegrade the chelant in the presence of metal ions representative of those found in the environment. Such a test simulates the environment encountered in a municipal waste treatment plant for screening the inherent biodegradability of non-volatile water-soluble compounds.

The modified Sturm test, in a similar manner contacts the chelant with a standardized culture of microorganisms. The evolution of carbon dioxide is used as a basis for determining microbial degradation when the test chelant is used as the sole carbon source.

N-[2-(carboxymethoxy)ethyl]-N-(carboxymethyl)glycine as a chelant is useful, for instance, in food products vulnerable to metal-catalyzed spoilage or discoloration; in cleaning and laundering products for removing metal ions, e.g. from hard water that may reduce the effectiveness, appearance, stability, rinsibility, bleaching effectiveness, germicidal effectiveness or other property of the cleaning agents; in personal care products like creams, lotions, deodorants and ointments to avoid metal-catalyzed oxidation and rancidity, turbidity, reduced shelf-like and the like; and in pulp and paper processing to enhance or maintain bleaching effectiveness. N-[2-(carboxymethoxy)ethyl]-N-(carboxymethyl) glycine can also be used in pipes, vessels, heat exchanges, evaporators, filters and the like to avoid or remove scaling; in pharmaceuticals; in metal working; in textile preparation, desizing, scouring, bleaching, dyeing and the like; in agriculture as in chelated micronutrients or herbicides; in polymerization or stabilization of polymers; in photography, e.g. in developers or bleaches; and in the oil field such as for drilling, production, recovery, hydrogen sulfide abatement and the like. The amount of chelating agent employed in the above noted applications are known in the art.

The use of N-[2-(carboxymethoxy)ethyl]-N-(carboxymethyl)glycine is particularly advantageous in hard-surface cleaners applications for the control of alkaline-earth metals, particularly calcium, and in preventing scaling. Typical applications for N-[2-(carboxymethoxy)-ethyl]-N-(carboxymethyl)glycine include the use in cleaning compositions suitable for hard-surface cleaning, such as certain automatic dishwashing agents and kitchen or bathroom soil removal and calcium soap removal from bathtub surfaces. When used in hard-surface cleaning compositions, N-[2-(carboxymethoxy) ethyl]-N-(carboxymethyl)glycine generally constitutes at least about 0.1 weight percent of the cleaning composition and typically less than about 25 percent of the cleaning composition. Preferably the hard-surface cleaning composition comprises about 0.1 to about 15 percent N-[2-(carboxymethoxy)ethyl]-N-(carboxymethyl)glycine, and more preferably about 0.5 to about 5 percent.

In addition to being biodegradable, it has been found that N-[2-(carboxymethoxy)ethyl]-N-(carboxymethyl)glycine can be used in hard-surface cleaning compositions free of organic solvents. This is particularly advantageous in that cleaning can be done without the concern for release of organic solvent into the environment.

Hard-surface cleaning compositions containing N-[2-(carboxymethoxy)ethyl]-N-(carboxymethyl)glycine are usually at an alkaline pH with a range of about 8 to about 14. Preferably the pH of the cleaning composition is from about 9 to about 13, and more preferably from about 10 to about 12.

In addition to N-[2-(carboxymethoxy)ethyl]-N-(carboxymethyl)glycine, hard surface cleaning compositions of the present invention can optionally contain additional additives well known in the art. For example, surface-active agents, are beneficial in a hard-surface cleaner.

Such surface active agents include water-soluble surfactants such as synthetic anionic, nonionic, cationic, amphoteric and zwitterionic surfactants and mixtures thereof. Exemplary surfactants include the alkyl benzene sulfates and sulfonates, paraffin sulfonates, olefin sulfonates, alkoxylated (especially ethoxylated) alcohols and alkyl phenols, amine oxides, sulfonates of fatty acids and of fatty acid esters, and the like, which are known in the detergency art. Preferably, such surfactants contain an alkyl group in about the $C_{10}$–$C_{18}$ range. Anionic surfactants are commonly used in the form of their sodium, potassium or triethanol ammonium salts. The nonionics advantageously contain from about 3 to about 17 ethylene oxide groups per mole of hydrophobic moiety. Representative cationic surfactants include quaternary ammonium compounds such as ditallow dimethyl ammonium chloride, and are preferably used in combination with nonionic surfactants. Preferred in the composition are about $C_{12}$–$C_{16}$ alkyl benzene sulfonates, about $C_{12}$–$C_{18}$ paraffin-sulfonates and the ethoxylated alcohols of the formula $RO(CH_2—CH_2O)n$, with R being a $C_{12}$–$C_{15}$ alkyl chain and n being a number from 6 to 10, and the ethoxylated alcohol sulfates of formula $RO—(CH_2—CH_2O)n—SO_3M$, with R being a $C_{12}$–$C_{18}$ alkyl chain, n is a number from about 2 to about 8, and M is H or an alkali metal ion.

Anionic surfactants are advantageously present at levels from about 0.3 percent to about 8 percent of the hard surface cleaning composition. Nonionic surfactants, are preferably used at levels between about 0.1 percent to about 6 percent by weight of the composition. Mixtures of surfactants are also useful.

Other optional ingredients include detergent builders within the skill in the art including nitrilotriacetate (NTA), polycarboxylates, citrates, water-soluble phosphates such as tri-polyphosphate and sodium ortho- and pyro-phosphates, silicates, ethylenediaminetetraacetate (EDTA), aminopolyphosphonates, and mixtures thereof.

Other optional additives for the hard surface cleaning compositions include detergent hydrotropes. Exemplary hydrotropes include urea, monoethanolamine, diethanolamine, triethanolamine and the sodium, potassium, ammonium and alkanol ammonium salts of xylene sulfonates, toluene sulfonates, ethylbenzene sulfonates and isopropylbenzene sulfonates.

The hard-surface cleaning compositions of the invention also optionally contain an abrasive material. The abrasive materials include water-insoluble, non-gritty materials known for their relatively mild abrasive properties. It is preferred that the abrasives used herein not be undesirably "scratchy". Abrasive materials having a Mohs hardness of no more than about 7 are preferred; while abrasives having a Mohs hardness of no more than about 3, are useful to avoid scratches on finishes such as aluminum or stainless steel. Suitable abrasives include inorganic materials, especially such materials as calcium carbonate and diatomaceous earth, as well as materials such as Fuller's earth, magnesium carbonate, China clay, actapulgite, calcium hydroxyapatite, calcium orthophosphate, dolomite and the like. The aforesaid inorganic materials can be described as "strong abrasives". Organic abrasives such as ureaformaldehyde, methyl methacrylate melamine-formaldehyde resins, polyethylene spheres and polyvinylchloride are advantageously used to avoid scratching on certain more delicate surfaces, such as plastic surfaces. Preferred abrasives have a particle size range of about 10–1000 microns and are preferably used at concentrations of about 5 percent to about 30 weight percent of the hard surface cleaning compositions.

Thickeners are preferably used to suspend the abrasives. Levels of thickener difficult to rinse from the cleaned surfaces are undesirable. Accordingly, the level is preferably less than about 2 percent, preferably from about 0.25 to about 1.5 percent. Exemplary thickeners include polyacrylates, xanthan gums, carboxymethyl celluloses, swellable smectite clay, and the like.

Soaps, especially soaps prepared from coconut oil fatty acids are also optionally included in the hard surface cleaners.

Optional components include components within the skill in the art to provide aesthetic or additional product performance benefits. Such components include perfumes, dyes, optical brighteners, soil suspending agents, detersive enzymes, gel-control agents, thickeners, freeze-thaw stabilizers, bactericides, preservatives, and the like.

The hard-surface cleaning compositions of the invention are advantageously in the form of liquid compositions, preferably aqueous compositions, including concentrates, containing as the essential ingredient N-[2-(carboxymethoxy)-ethyl]-N-(carboxymethyl)glycine Preferably a surfactant is also present, more preferably in a concentration that corresponds to from about 2 to about 6 percent surfactant. Concentrated liquid compositions preferably contain from about 6 to about 10 percent surfactant. Alternatively, the compositions herein are in the form of creamy scouring cleansers, preferably containing an abrasive material, surface-active agent, and N-[2-(carboxymethoxy)ethyl]-N-(carboxymethyl)glycine.

The cleaning compositions can be packaged in a container that comprises a means for creating a spray, e.g., a pump, aerosol propellant or spray valve. The composition can be thus conveniently applied to the surface to be cleaned by conventional means, such as wiping with a paper towel or cloth, without the need for rinsing.

The following examples are offered to illustrate but not limit the invention. Percentages, ratios and parts are by weight unless stated otherwise.

EXAMPLE 1

The Stepwise Procedure for the Synthesis of N-[2-(carboxymethoxy) ethyl]-N-(carboxymethyl)glycine Synthesis of [2-(cyanomethylamino)ethoxy]acetic acid (III): In a 300 mL beaker was placed 5.78 g (57 mmol) of 3-morpholinone (I), 50% (w/w)sodium hydroxide (5.02 g, 63 mmol), 100 mL of water and a magnetic stir bar. The resulting solution was heated for 30 min at a gentle boil then cooled to room temperature. While the solution was stirring at room temperature, the glycolonitrile (40 percent aqueous, 8.13 g, 57 mmol) was added dropwise. The solution was stirred at room temperature for 1 h. at which time a $^{13}C$ NMR indicated that the reaction was complete. $^{13}C$ NMR ($D_2O$): δ 50.3, 53.4, 119.4, 179.7, 180.9 ppm.

Synthesis of N-[2-(carboxymethoxy)ethyl]glycine (V): The solution of [2-(cyanomethylamino)ethoxy]acetic acid (III) obtained above was carried on to the hydrolysis step without purification by the addition of 5.02 g of 50 percent (w/w) NaOH. After stirring at room temperature for 30 min, the solution was brought to a boil to liberate the ammonia and heating continued until no ammonia was etected. $^{13}C$ NMR ($D_2O$): δ 50.2, 55.0, 72.4, 72.6,181.0, 182.5 ppm.

Synthesis of N-[2-(carboxymethoxy)ethyl]-N-(cyanomethyl)glycine (VII): To a solution of N-[2-(carboxymethoxy)ethyl]glycine (V), which was at room temperature, was added glycolonitrile (40 percent aqueous, 5.02 g, 57 mmol) dropwise. After stirring for 30 min at room temperature the $^{13}C$ NMR indicated that the reaction was complete. The nitrile intermediate was carried on to the next step without further purification. $^{13}C$ NMR ($D_2O$): δ 44.9, 55.7, 61.1, 70.0, 72.5, 119.4, 180.2, 180.8 ppm Hydrolysis of N-[2-(carboxymethoxy)ethyl]-N-(cyanomethyl)glycine (VII) to N-[2-(carboxymethoxy) ethyl]-N-(carboxymethyl)glycine (IX): To an aqueous solution of N-[2-(carboxymethoxy)ethyl]-N-(cyanomethyl) glycine (VII) was added 5.02 g of 50 percent (w/w) NaOH. After stirring at room temperature for 3 h the hydrolysis was complete. The solution was brought to a boil to liberate the ammonia and heating continued until no further ammonia was detected. $^{13}C$ NMR ($D_2O$): δ 57.1, 62.0, 70.0, 72.2, 180.9, 182.5 ppm.

EXAMPLE 2

Synthesis of N-[2-(carboxymethoxy)ethyl]-N-(carboxymethyl)glycine

A 250 mL beaker equipped with a magnetic stirring bar was charged with 4.5 g (0.045 mol) of 3-morpholinone, 100 mL of water and 50% sodium hydroxide (w/w, 11.2 g, 5.6 g active 0.14 mol). The solution was heated to a boil, then the first equivalent of glycolonitrile (40% w/w, 6.42 g, 2.57 g active 0.045 mol) was added dropwise. Upon completion of the addition, the solution was boiled until the release of ammonia was no longer detected with pH paper. The second equivalent of glycolonitrile (40% w/w, 6.42 g, 2.57 g active 0.045 mol) was slowly added dropwise to the boiling solution. The resulting solution was then heated to a gentle boil to remove the ammonia. The resulting solution was heated an additional 0.5 h. A $^{13}$C NMR indicated that the reaction was partially complete. To drive the reaction to completion, an additional amount of 50% sodium hydroxide (0.36 g, 4.5 mmol) was added, followed by the slow, dropwise addition of 40% glycolonitrile (0.64 g 4.5 mmol). The process was repeated a second time to eventually drive the reaction to completeness. $^{13}$C NMR (D$_2$O): δ 57.2, 61.9, 70.2, 72.4, 181.0, 182.7 ppm.

EXAMPLE 3

The procedure of ASTM D2667 is used to determine the inherent biodegradablity of N-[2-(carboxymethoxy)ethyl]-N-(carboxymethyl)glycine.

Copper titration value is used to measure the extent of biodegradation of the chelating agents during the procedure. Titration is performed using ammonium purpurate (indicator for complexometric titration, commercially available from Aldrich Chemical Co., Inc. under the trade designation Murexide) at approximately pH 8, and using sodium acetate as buffer. Titration of 2 g N-[2-(carboxymethoxy)ethyl]-N-(carboxymethyl)glycine (0.009 mmol) in 100 mL water with 0.01 molar copper chloride gives an endpoint of 0.99 mL, representing a 1:1 chelation of copper. Analysis is performed daily for a period of 28 days.

Results of the biodegradation screening are given in Table I below:

TABLE I

| Compound | Time for greater than 80% loss of chelation |
| --- | --- |
| NTA (std.) | 3 days |
| (IX) | 30 |
| EDTA (std.) | greater than 40 days |

A control is used to verify the absence of interfering chelating substances in the test.

The results of the biodegradability test show that N-[2-(carboxymethoxy)ethyl]-N-(carboxymethyl)glycine (IX) is inherently biodegradable and could be expected to be utilized by organisms in a municipal treatment facility after an acceptable acclimation period.

EXAMPLE 4

Calcium Chelation Capacity of N-[2-(carboxymethoxy)ethyl]-N-(carboxymethyl)glycine The applicability of N-[2-(carboxymethoxy)ethyl]-N-(carboxymethyl)glycine for use in hard surface cleaners, is measured by the calcium oxalate titration.

For titration with calcium oxalate, N-[2-(carboxymethoxy)ethyl]-N-(carboxymethyl)glycine (between 1 to 2 millimoles) is placed in a 60 mL beaker. After the addition of 30 mL deionized water and 5 mL of a 3% ammonium oxalate solution, the pH is slowly brought to about 10 by the addition of 20% sodium hydroxide while stirring. The pH is then adjusted to about 11.6 with sodium hydroxide and the solution is titrated with 0.1 M CaCl$_2$ to the first permanent turbidity. The chelation valve is then determined from the mL of titrant used based on the following calculation.

Chelation Value=(mL titrant used×molarity titrant)×100 mg CaCO$_3$ per mmole÷sample wt. in grams×activity of sample (as acid form)

The chelation value is the mg of CaCO$_3$ that can be chelated by one active gram of a chelant, such as N-[2-(carboxymethoxy)ethyl]-N-(carboxymethyl)glycine (IX).

The turbidity produced in the oxalate titration is due to the formation of calcium oxalate. The results for the titration of N-[2-(carboxymethoxy)ethyl]-N-(carboxymethyl)glycine in the presence of oxalate is compared with iminodiacetic acid (IDA) and given in Table II below.

TABLE II

| OXALATE TITRATION | |
| --- | --- |
| Chelant | Chelation Value |
| IDA | 1 |
| (IX) | 423 |

The results from the oxalate titration showed that N-[2-(carboxymethoxy)ethyl]-N-(carboxymethyl)glycine (IX) exhibits a chelation value far superior to IDA. Therefore, for applications requiring calcium control, such as in hard surface cleaners, N-[2-(carboxymethoxy)ethyl]-N-(carboxymethyl)glycine (can be used as a more biodegradable substitute for EDTA.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A compound represented by the following formula:

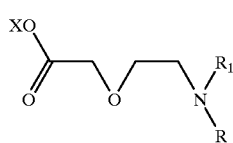

X wherein R and R$_1$ independently represent H, —CH$_2$CN or —CH$_2$CO$_2$X, with the proviso that R and R$_1$ can not be both H or —CH$_2$CO$_2$X; and X represents hydrogen, an alkali metal or alkaline earth metal.

2. A compound of claim 1 represented by the following formula:

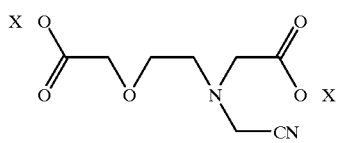

VII wherein X represents hydrogen, an alkali metal or alkaline-earth metal.

3. A compound of claim 2 which is N-[2-(carboxymethoxy)ethyl]-N-(cyanomethyl)glycine.

4. A compound of claim 1 represented by the following formula:

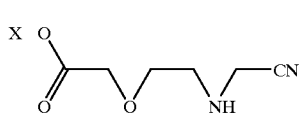 III
wherein X represents hydrogen, an alkali metal or alkaline-earth metal.
5. A compound of claim 4 which is [2-(cyanomethylamino)ethoxy]acetic acid.
6. A compound of claim 1 represented by the following formula:
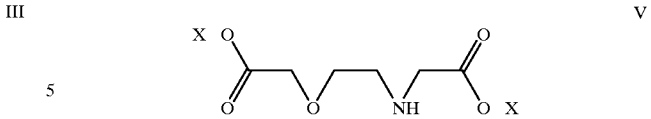 V
wherein X represents hydrogen, an alkali metal or alkaline earth metal.
7. A compound of claim 6 which is N-[2-(carboxymethoxy) ethyl]glycine.
* * * * *